US008474122B2

(12) United States Patent
Melsheimer

(10) Patent No.: US 8,474,122 B2
(45) Date of Patent: Jul. 2, 2013

(54) APPARATUS FOR COMPRESSING AN EXPANDABLE MEDICAL DEVICE

(71) Applicant: Cook Medical Technologies LLC, Bloomington, IN (US)

(72) Inventor: Jeffry S. Melsheimer, Springville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/676,522

(22) Filed: Nov. 14, 2012

(65) Prior Publication Data

US 2013/0074712 A1    Mar. 28, 2013

Related U.S. Application Data

(63) Continuation of application No. 13/235,006, filed on Sep. 16, 2011, which is a continuation of application No. 11/776,253, filed on Jul. 11, 2007, now Pat. No. 8,020,277.

(60) Provisional application No. 60/833,986, filed on Jul. 28, 2006, provisional application No. 60/861,148, filed on Nov. 27, 2006.

(51) Int. Cl.
*B21D 39/00* (2006.01)
*B23P 19/00* (2006.01)

(52) U.S. Cl.
USPC .............................. 29/508; 29/751

(58) Field of Classification Search
USPC .............. 29/508, 525, 235, 283.5, 282, 237, 29/751; 604/159, 510; 623/1.12; 72/402, 72/416, 357, 409, 409.01; 606/1
See application file for complete search history.

(56) References Cited

U.S. PATENT DOCUMENTS

| 6,568,235 | B1 | 5/2003 | Kokish |
| 6,629,350 | B2 | 10/2003 | Motsenbocker |
| 6,726,713 | B2 | 4/2004 | Schaldach et al. |
| 6,769,161 | B2 | 8/2004 | Brown et al. |
| 6,840,081 | B2 | 1/2005 | Kokish |
| 6,915,560 | B2 | 7/2005 | Austin |
| 7,207,204 | B2 | 4/2007 | Weber et al. |
| 8,104,321 | B2 * | 1/2012 | Serrano et al. .................. 72/402 |
| 2002/0138966 | A1 | 10/2002 | Motsenbocker |
| 2002/0163104 | A1 | 11/2002 | Motsenbocker et al. |
| 2003/0056360 | A1 | 3/2003 | Brown et al. |
| 2003/0150250 | A1 | 8/2003 | Shortt |
| 2004/0128818 | A1 | 7/2004 | Motsenbocker |
| 2005/0115336 | A1 | 6/2005 | Motsenbocker et al. |
| 2006/0213049 | A1 | 9/2006 | Serrano et al. |

(Continued)

FOREIGN PATENT DOCUMENTS

WO    WO 2005/047839 A2    5/2005

*Primary Examiner* — John C Hong
(74) *Attorney, Agent, or Firm* — Brinks Hofer Gilson & Lione

(57) ABSTRACT

Systems and methods for compressing a medical device, such as a self-expanding stent, and loading the compressed medical device into a sheath are disclosed. A plurality of moveable blades are disposed about a central axis and form a radially contractible aperture which receives the device. An operating mechanism moves the blades between an expanded configuration and a radially contracted configuration. A subset of the blades is independently moveable in an axial direction with respect to other of the blades while the blades are in a contracted configuration.

20 Claims, 14 Drawing Sheets

U.S. PATENT DOCUMENTS

2006/0216404 A1 9/2006 Seyler et al.
2006/0265855 A1 11/2006 Stenzel
2007/0056346 A1 3/2007 Spenser et al.

* cited by examiner

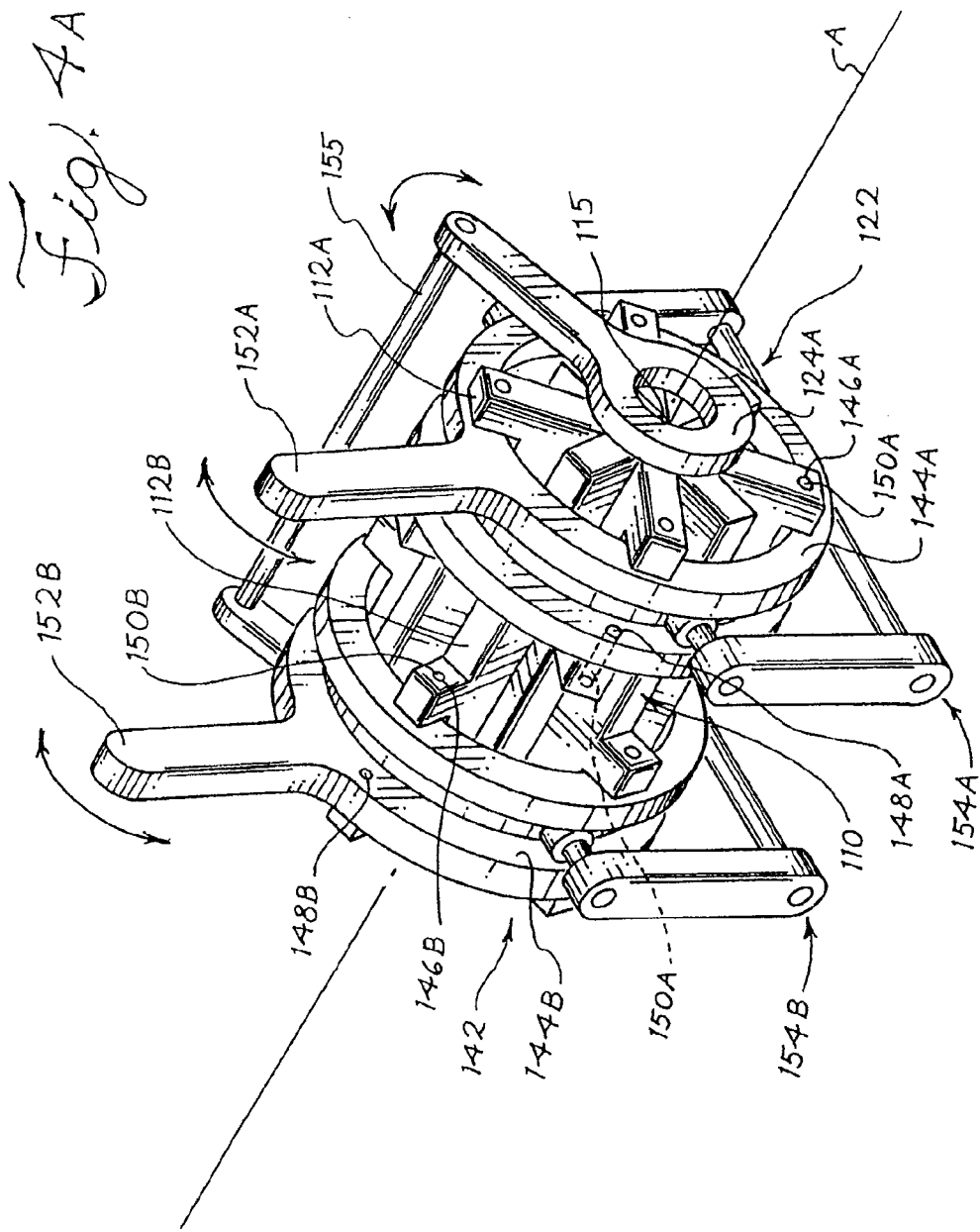

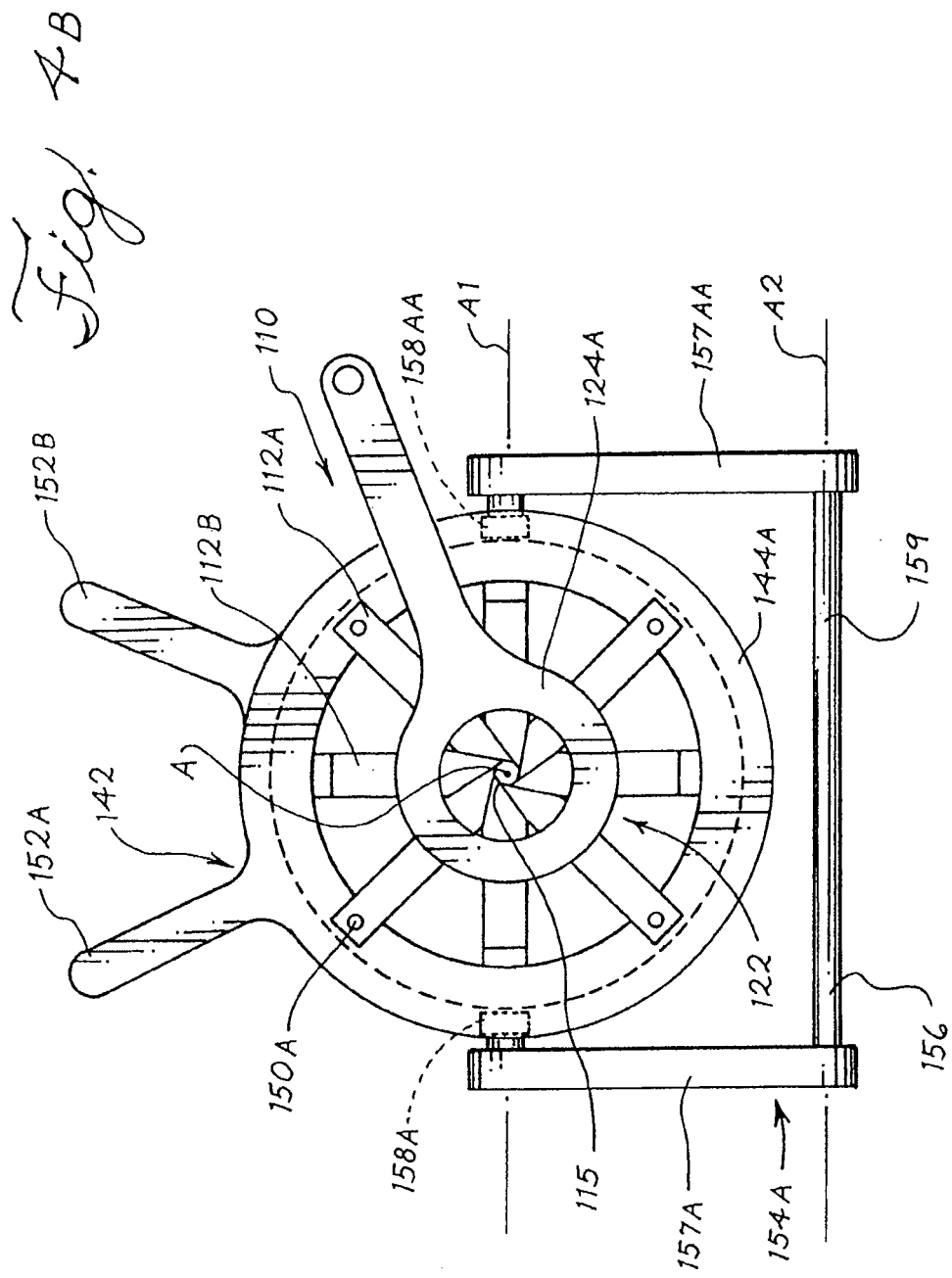

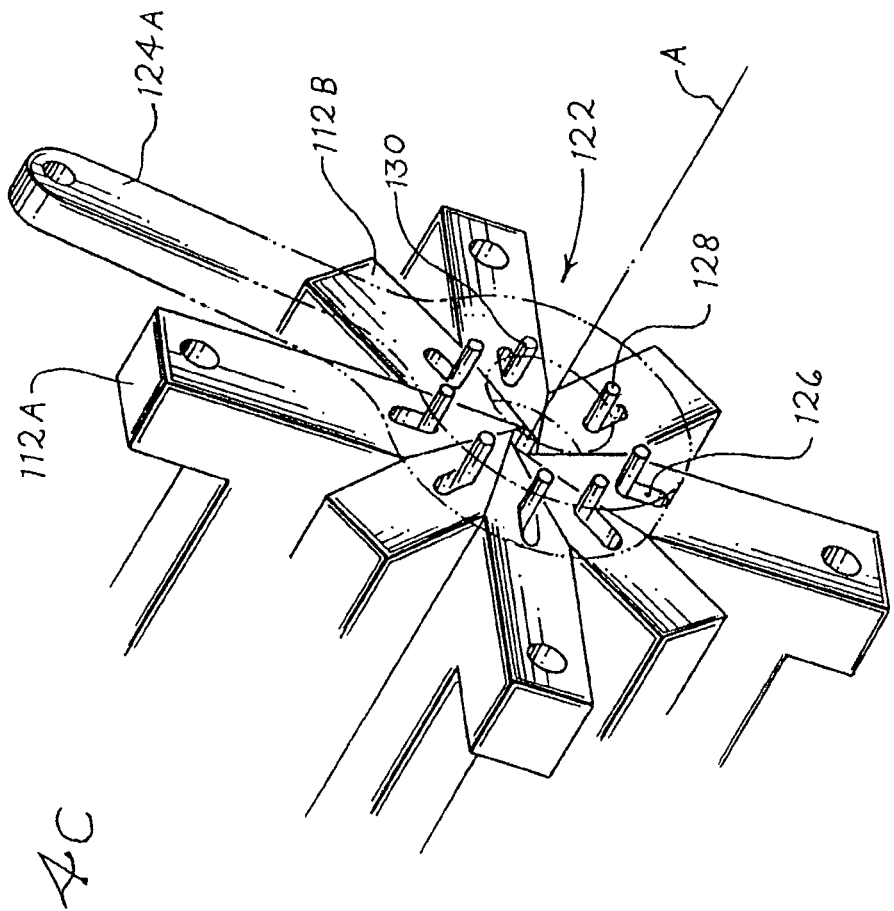

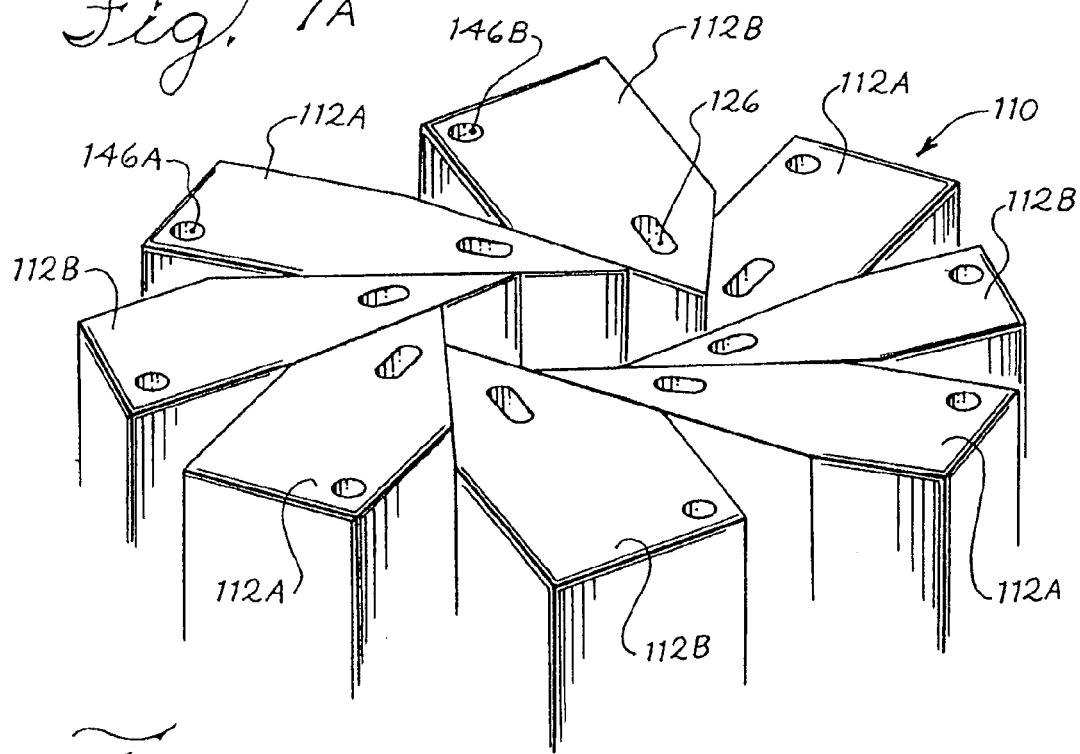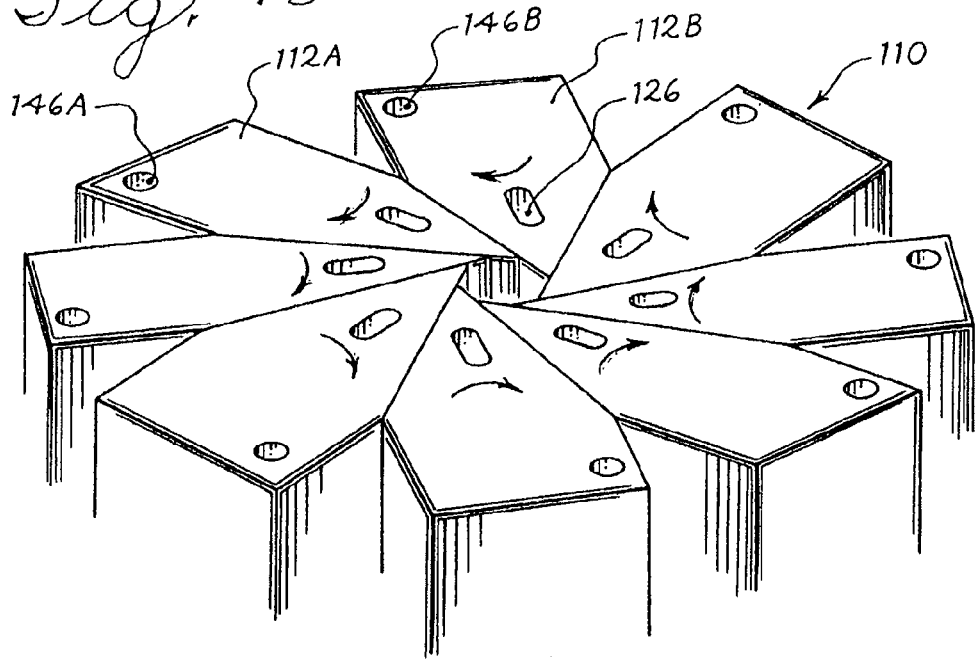

APPARATUS FOR COMPRESSING AN EXPANDABLE MEDICAL DEVICE

CROSS-REFERENCE TO RELATED APPLICATIONS

This application is a continuation under 37 C.F.R. §1.53(b) of U.S. Utility patent application Ser. No. 13/235,006, filed Sep. 16, 2011, which is a continuation of Utility patent application Ser. No. 11/776,253, filed Jul. 11, 2007, which issued Sep. 20, 2011 as U.S. Pat. No. 8,020,277, which claims the benefit of the filing dates under 35 U.S.C. §119(e) of U.S. Provisional Patent Application Ser. No. 60/833,986, filed Jul. 28, 2006, and of U.S. Provisional Patent Application Ser. No. 60/861,148, filed Nov. 27, 2006, each of which is hereby incorporated by reference.

BACKGROUND OF THE INVENTION

1. Field of the Invention

This invention relates to a system and an apparatus for, and a method of compressing an expandable medical device, for example, a stent, and for loading the compressed device into a sheath.

2. Description of Related Art

Intraluminally delivered expandable medical devices have been used to treat damaged or diseased body lumens. Many structures and functions are known in the art. For example, expandable medical devices, namely stent grafts, have been used to treat aortic and thoracic abdominal aneurysms. Expandable medical devices include, but are not limited to, stents, stent grafts, and vena cava filters.

Expandable medical devices may be delivered and deployed using various techniques. For example, a compressed, self-expanding stent graft may be intraluminally delivered and deployed using a catheter delivery system. A stent graft is placed in a radially reduced configuration within the lumen of a catheter or sheath. The catheter is inserted into the vasculature, whereupon the stent graft is delivered to the deployment site. Once the stent graft is properly positioned, the sheath is withdrawn from the stent graft so that the stent graft is allowed to radially expand within the body lumen.

Various apparatuses have been provided for compressing an expandable medical device and for loading the compressed device into a sheath. Examples of such apparatuses are described in U.S. Pat. No. 6,629,350, entitled "Stent Crimping Apparatus and Method," which is herein incorporated by reference. Typically, a compressor is provided that includes a plurality of blades that forces the device into a compressed configuration. Once the device is compressed, a pusher is used to force the device out of the compressor and into the sheath.

Such a pusher must provide sufficient force to overcome the frictional resistance that can build up between the medical device and the blades. This resistance can be particularly large where the medical device is self-expanding and is biased against the blade surfaces. Prior art apparatuses are effective for compressing and loading short devices and for compressing and loading relatively rigid devices that possess a column strength that is sufficient to withstand the force exerted by the pusher. Longer and/or axially flexible medical devices may present challenges where they do not possess sufficient column strength, and can buckle or crush under the force of the pusher.

SUMMARY

According to an aspect of the present invention, a system for compressing and loading an expandable medical device into a sheath is provided and comprises an array of moveable blades. The blades are radially disposed about a central axis and form a radially contractible aperture. The blade array is configured to receive and compress an expandable medical device within the aperture. The array may comprise two or more independently moveable groups of blades. For example, the array may comprise at least a first plurality of blades and a second plurality of blades, where the first plurality of blades is independently moveable with respect to the second plurality of blades.

The first plurality of blades may be slidably disposed along the central axis in a first and second direction with respect to the second plurality of blades and/or the second plurality of blades may be slidably disposed along the central axis in a first and second direction with respect to the first plurality of blades. Alternatively, or additionally, the first plurality of blades may be moveable radially inwardly and outwardly with respect to the second plurality of blades and/or the second plurality of blades may be moveable radially inwardly and outwardly with respect to the first plurality of blades.

A compressor system may comprise a first operating mechanism for selectively moving the first plurality of blades independently with respect to the second plurality of blades. Another compressor system may comprise a first operating mechanism for selectively moving the first and second pluralities of blades between an expanded configuration and a contracted configuration. The system may additionally comprise a second operating mechanism for selectively moving the first plurality of blades independently with respect to the second plurality of blades. The second operating mechanism may be configured to move the first plurality of blades radially inwardly and outwardly with respect to the second plurality of blades and/or vice versa. Alternatively, the second operating mechanism may be configured to slide the first plurality of blades along the central axis in a first and second direction with respect to the second plurality of blades and/or vice versa.

A compressor system of the present invention is particularly useful for compressing and loading a self-expanding medical device into a sheath. When the medical device is compressed within the first aperture by the first plurality of blades, any engagement between the medical device and the blades will tend to limit the ability of the medical device to slide within the aperture. One of the goals of the present invention is to regulate or control the engagement between the blades and the medical device. Accordingly, the first plurality of blades may be configured to disengage from the medical device when the device is held by the second plurality of blades. Additionally, or alternatively, the second plurality of blades may be configured to disengage from the medical device when the device is held by the first plurality of blades.

According to yet another aspect of the present invention, a method of compressing and loading an expandable medical device into a sheath is provided. An exemplary method may include providing a compressor that includes an array of moveable blades that are radially disposed about a central axis and that form a radially contractible aperture. The blade array may include two or more groups of blades, for example a first plurality of blades and a second plurality of blades.

The method may further comprise the steps of compressing an expandable medical device within the aperture, and moving the medical device within the aperture by selectively moving the first plurality of blades independently with respect to the second plurality of blades.

The moving step may further comprise any of the steps of pushing the medical device within the aperture with a pusher; moving the first plurality of blades along the central axis in a first direction while the medical device is held by the first plurality of blades; selectively disengaging and engaging the first plurality of blades from the medical device while the medical device is held by the second plurality of blades; and selectively disengaging and engaging the first plurality of blades from the medical device while the medical device is held by the second plurality of blades.

An exemplary method may include the following steps:
i. moving the first plurality of blades along the central axis in a first direction while the medical device is held by the first plurality of blades;
ii. disengaging the first plurality of blades from the medical device while the medical device is held by the second plurality of blades;
iii. moving the first plurality of blades along the central axis in a second direction;
iv. engaging the first plurality of blades with the medical device; and
v. disengaging the second plurality of blades from the medical device while the medical device is held by the first plurality of blades.

The preceding steps may be repeated one or more times to transfer the medical device into a sheath that is aligned with the aperture.

BRIEF DESCRIPTION OF THE DRAWINGS

FIG. 4A is a perspective view of a compressor system according to an aspect of the present invention;

FIG. 4B is a schematic front view of the compressor system of FIG. 4A;

FIG. 4C is an enlargened perspective view of an inner hub of the compressor system of FIG. 4A;

FIGS. 7A-G illustrate partial perspective views of an exemplary compressor system of the present invention, in various stages of use corresponding with FIGS. 6A-G.

DETAILED DESCRIPTION OF THE PREFERRED EMBODIMENTS

Throughout the specification, the term "medical device" shall mean any device that is configured to support, repair, or replace a body part or function of that body part. It can also mean a device that enhances or adds functionality to a physiological system. A stent is an example of a medical device.

The term "stent" means any device or structure that provides or is configured to provide rigidity, expansion force, or support to a body part, for example, a diseased or otherwise compromised body lumen. A stent may be bare, or it may include a covering or graft material. Thus the term "stent" includes devices such as stent grafts. Suitable coverings or graft materials for stents include biocompatible polymers, such as poly(ethylene terephthalate), polylactide, polyglycolide and copolymers thereof; fluorinated polymers, such as polytetrafluoroethylene (PTFE), expanded PTFE and poly (vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments.

The term "expandable" describes an object, device, or structure that is capable of being expanded, either by virtue of its own resilience, or upon the application of an external force. Expandable stents include both self-expanding and balloon-expandable devices. Self-expanding stents can be made of stainless steel, materials with elastic memory properties, such as NITINOL, or any other suitable material. Exemplary self-expanding stents include Z-STENTS® and ZILVER® stents, which are available from Cook Incorporated, Bloomington, Ind. USA. Balloon-expandable stents may be made, for example, of stainless steel (typically 316LSS, CoCr, etc.). Hybrid stents may be provided by combining one or more self-expanding stents or stent portions with one or more balloon-expandable stents or stent portions.

Figure 1:
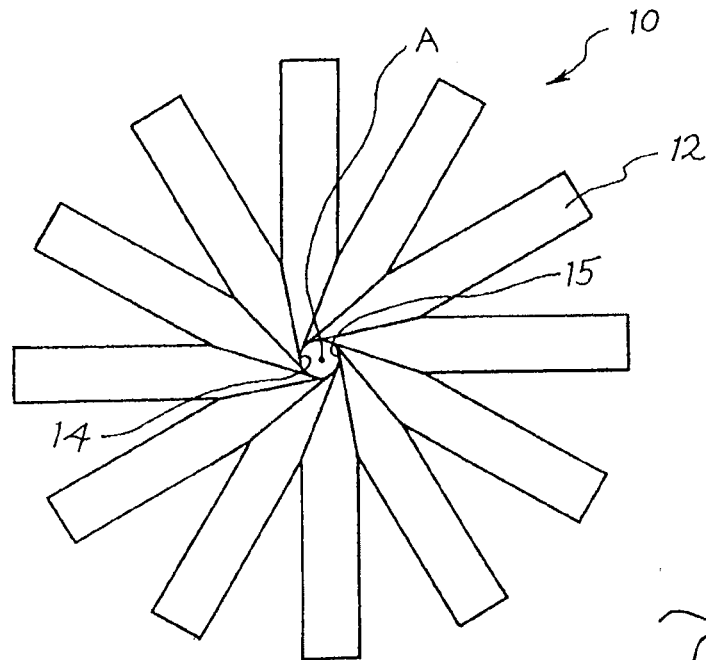
FIG. 1 is a schematic front view of a blade array for a stent compressor, shown in an expanded configuration.
Figure 2:
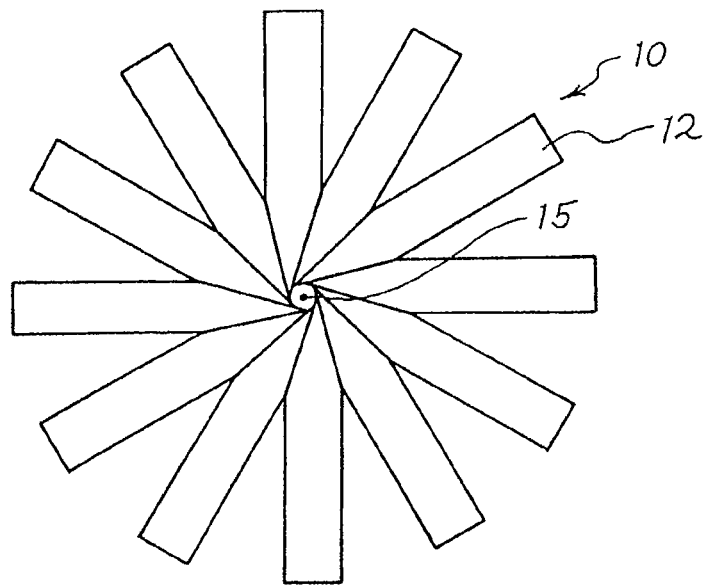
FIG. 2 is a schematic front view of the blade array of FIG. 1, shown in a contracted configuration.

FIGS. 1 and 2 illustrate a blade array 10 for a stent compressor. The blade array 10 includes a plurality of moveable compressor blades 12. The blades 12 are arranged to form an iris 14 that defines a contractible aperture 15. The aperture 15 has a central axis A.

The blade array 10 is configured to receive and compress an expandable medical device, such as a stent, within the aperture 15. The blades 12 are moveable between an expanded configuration, as shown in FIG. 1, and a contracted configuration, as shown in FIG. 2. In the expanded configuration, the radius of the aperture 15 is generally equal to or greater than an expanded radius of the medical device so that the medical device can be loaded into the compressor. In the contracted configuration, the radius of the aperture 15 is generally less than the expanded radius of the medical device.

The blade array 10 shown in FIGS. 1 and 2 comprises twelve blades 12. Blade arrays 10 can comprise a greater or a fewer number of blades, for example, as few as three, or more than twelve blades 12. Generally, as the number of blades 12 increases, the contour of the aperture 15 will become smoother, and the contact area between the blades 12 and the medical device will increase, thereby increasing the area of frictional contact between the compressor blades 12 and the medical device.

Figure 3A:
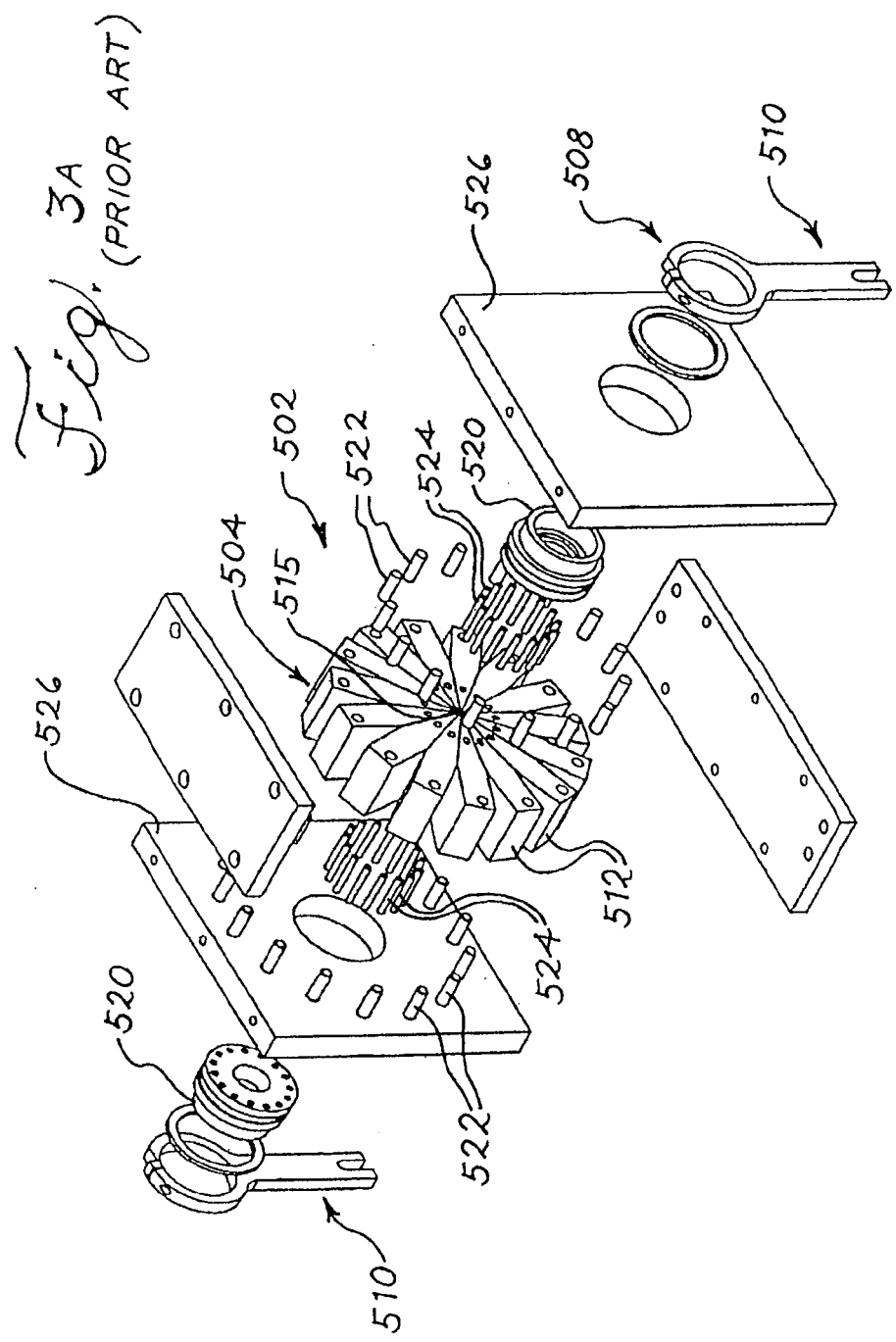
FIGS. 3A-3C illustrate various views of a prior art compressor.
Figure 3B:
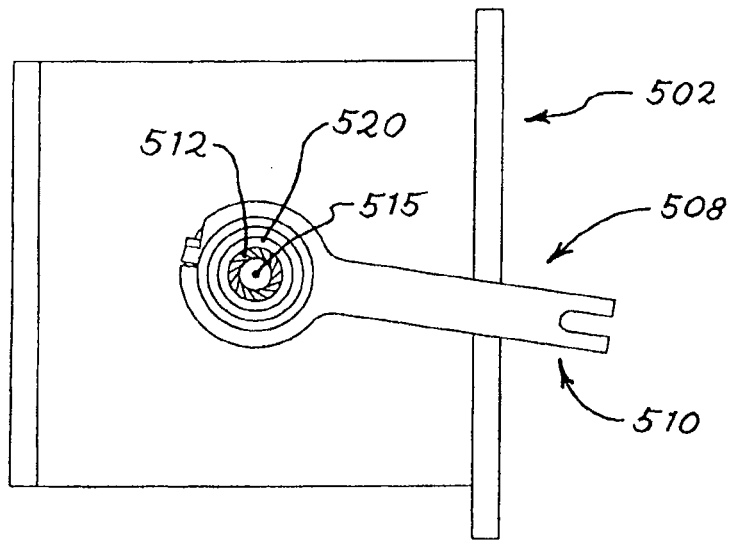
Figure 3C:
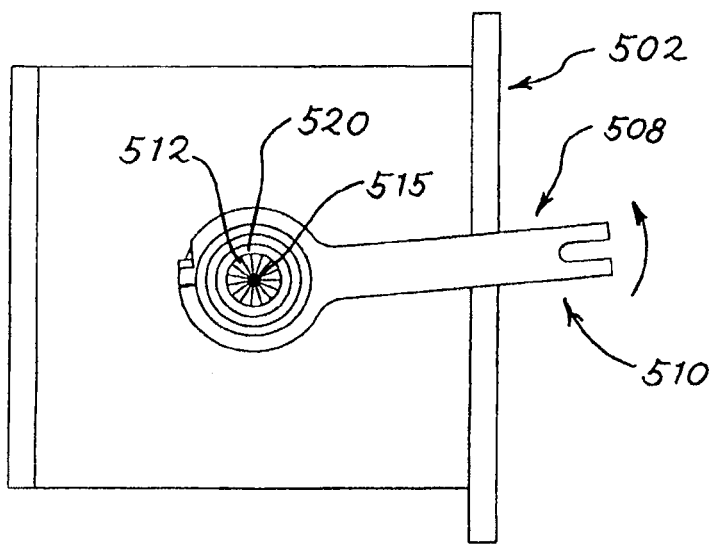

FIGS. 3A-3C illustrate an example of a prior art compressor that is described in U.S. Pat. No. 6,629,350, entitled "Stent Crimping Apparatus and Method." The compressor comprises a crimp head 502 that includes an array 504 of moveable blades 512. The crimp head 502 further comprises a set of drive hubs 520, pivot pins 522, drive pins 524, and stationary base plates 526. Each of the blades 512 is pivotally connected to the stationary base plates 526 via pivot pins 522 that are disposed within cylindrical bores formed in the blades 512 and in each of the base plates 526. Each of the blades 512 is connected to the drive hubs 520 via drive pins 524 that are disposed within cylindrical bores in each of the drive hubs 520 and in drive slots formed in the blades 512. The drive slots have a cylindrical configuration with a cross-section that is slightly radially elongated, rather than a circular cross-section.

The crimp head 502 is actuated by a drive mechanism 508 which includes a pair of rotation arms 510, each connected to a respective drive hub 520. The rotation arms 510 are driven in a synchronized manner to rotate the drive hubs 520, thereby moving the blade array 504 between an expanded configuration and a contracted configuration.

FIG. 3B shows the stent compressor of FIG. 3A in an expanded configuration, wherein the aperture 515 is expanded and is capable of receiving a stent. FIG. 3C shows the stent compressor of FIG. 3A in a contracted configuration, wherein the aperture 515 is reduced. The blades 512 move between the expanded and contracted configuration by rotating the drive hubs 520 via rotation arms 510.

Prior art compressors, such as the one described in U.S. Pat. No. 6,629,350 are configured so that all of the blades in the blade array move in collaboration—the blades are coupled so that movement of each blade is coordinated with the movement of all of the other blades. Accordingly, prior art compressors do not permit independent movement of separate portions or groups within the blade array.

FIGS. 4A-4C illustrate a new compressor system. The compressor system is specially configured to receive and compress an expandable medical device, such as a stent, and comprises a blade array 110 having two or more independently moveable groups of blades. Such a system may be provided by converting a suitable commercially available compressor. Suitable compressors include Models SC100 and SC900, sold by Machine Solutions, Inc. of Flagstaff, Ariz.

The system shown in FIGS. 4A-4C comprises an array 110 of moveable compressor blades, arranged to form a contractible aperture 115. The array 110 includes a first plurality of blades 112A and a second plurality of blades 112B. The blades 112A, 112B are radially disposed about a common central axis A and are moveable between an expanded configuration and a contracted configuration. When the blades 112A, 112B are in the expanded configuration, an expandable medical device, (not shown) may be inserted into the aperture 115. In the contracted configuration, the blades 112A, 112B hold the device in a contracted configuration.

Each of the blades 112A, 112B in the blade array may be coupled to an inner hub mechanism 122. The inner hub mechanism 122 shown in the figures includes a first hub 124A and a second hub (hidden). As shown in FIG. 4C, each of the blades 112A, 112B may have a pair of inner elongated slots 126 (only one of the pairs of slots is visible in the figures). Each slot 126 has a cylindrical configuration with a cross-section that is radially elongated. The inner slots 126 are arranged in circular patterns about the central axis A. The first hub 124A and the second hub (hidden) of the inner hub mechanism 122 may each have a plurality of cylindrical bores 128 (only one of the pluralities of bores is visible in the figures). Inner pins 130 (only one of the pairs of pins is visible in the figures) couple the blades 112A, 112B to the inner hub mechanism 122 via slots 126 and corresponding bores 128. The pins 130 may be friction fitted with the bores 128 and are configured to move radially and axially within the slots 126.

In an alternative embodiment, each of the blades 112 may have an inner cylindrical bore, rather than an elongated slot, and each of the first and second hubs of the inner hub mechanism 122 may have a corresponding elongated slot.

Each of the blades 112A, 112B may be coupled to an outer hub mechanism 142. The outer hub mechanism 142 shown in the figures includes a first hub 144A and a second hub 144B. Each of the blades 112A, 112B may have an outer cylindrical bore 146A, 146B. Outer bores 146A, 146B are arranged in circular patterns about the central axis A and are disposed radially outwardly from inner slots 126. The first outer hub 144A has a plurality of cylindrical bores 148A, each corresponding with a bore 146A in the first plurality of blades 112A. Likewise, the second outer hub 144B has a plurality of cylindrical bores 148B, each corresponding with a bore 146B in the second plurality of blades 112B. The first plurality of blades 112A is coupled to the first hub 144A via pins 150A disposed in bores 146A and 148A, and the second plurality of blades 112B is coupled to the second hub 144B via pins 150B disposed in bores 146B and 148B.

To move the blades 112A, 112B between an expanded and a contracted configuration, the inner hubs 124A, 124B (hidden) may be rotated while holding the outer hubs 144A, 144B stationary. The system may comprise a control member, such as the tie bar 155 shown in FIG. 4A, for synchronizing the rotation of the inner hubs 124A, 124B. When the inner hubs 124A, 124B are rotated, each inner pin 130 moves in an arc about the central axis A and each blade 112A, 112B pivots within a respective outer hub 144A, 144B about an axis defined by a respective outer pin 150A, 150B. As the blades 112A, 112B pivot, the radius of the aperture 115 increases or decreases, depending on the direction of rotation of hubs 124A, 124B.

Alternatively, the blades 112A, 112B can be moved between the expanded and contracted configurations by rotating the first and second outer hubs 144A, 144B while holding the first and second inner hubs 124A, 124B stationary.

In an alternative embodiment of the present invention, the first and second pluralities of blades 112A, 112B may each be coupled to both the first and second outer hubs 144A, 144B. The first plurality of blades 112A may be coupled only to the first inner hub 124A, and the second plurality of blades 112B may be coupled only to the second inner hub 124B (hidden). To move the blades 112A, 112B between expanded and contracted configurations, the outer hubs 144A, 144B may be rotated together while holding the inner hubs 124A, 124B stationary, or vice versa.

Figures 5, 6A:
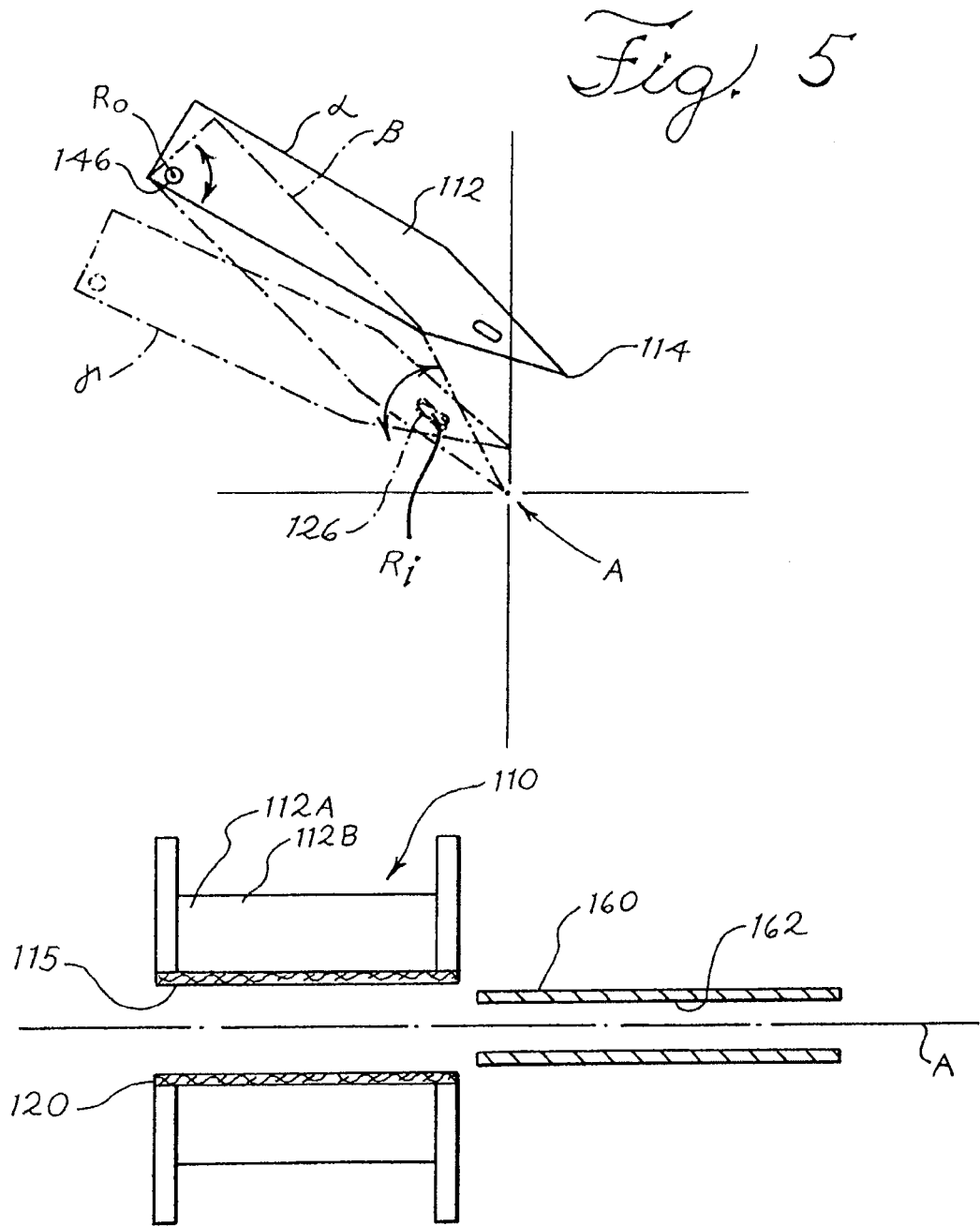
FIG. 5 illustrates movements of a compressor blade according to an aspect of the present invention.
FIGS. 6A-G illustrate cross-sectional schematic views of an exemplary compressor system of the present invention, in various stages of use.

The movement of a blade of the system shown in FIGS. 4A-4C is illustrated in FIG. 5. The expanded configuration of the blade is indicated by the position α and the contracted configuration of the blade is indicated by the position β. The blade moves between positions α and β by pivoting about an axis Ro corresponding with outer bore 146. The blade 112 moves along an arc such that the distal end 114 swings towards or away from the central axis A.

In the system shown in FIGS. 4A-4C, the outer hub mechanism 142 decouples the first plurality of blades 112A and the second plurality of blades 112B. Accordingly, the blades 112A, 112B may have radial and axial freedom of movement, unlike the blades in prior art stent compressors. The first and second pluralities of blades 112A, 112B can therefore be operated independently of each other. For example, the outer hubs 144A, 144B can be rotated independently to move the first plurality of blades 112A radially inwardly and outwardly with respect to the second plurality of blades 112B and vice versa. Further, blades 112A, 112B can move along the central axis A independently of one another by moving the outer hubs 144A, 144B axially with respect to each other.

The system shown in FIGS. 4A-4C includes first and second rotation arms 152A, 152B that are coupled to the first and second outer hubs 144A, 144B respectively. The first rotation arm 152A can be operated to selectively rotate the first outer hub 144A with respect to the second outer hub 144B. Similarly, the second rotation arm 152B can be operated to selectively rotate the second outer hub 144B with respect to the first outer hub 144A.

Rotation of the first outer hub 144A with respect to the second outer hub 144B causes each outer pin 150A to move in an arc about the central axis A and each blade 112A to pivot within the inner hubs 124A, 124B (not shown) about an axis defined by a respective inner pin 130. As the blades 112A pivot, they swing radially towards or away from the central axis A and radially inwardly or outwardly with respect to the second plurality of blades 112B. Likewise, rotation of the second outer hub 144B with respect to the first outer hub 144A causes each of the outer pins 150B to move in an arc about the central axis A and each of the second plurality of blades 112B to pivot within the inner hubs 124A, 124B about an axis defined by a respective inner pin 130. As the blades 112B pivot, they swing radially towards or away from the central axis and radially inwardly or outwardly with respect to the first plurality of blades 112A.

FIG. 5 shows the movement of a blade between a contracted configuration β and a retracted configuration γ as described above. The blade 112 moves between positions β and γ by pivoting about an axis Ri corresponding with inner slot 126. The blade 112 moves along an arc such that the distal end 114 swings towards or away from the central axis A.

According to an aspect of the invention, a compressor system may optionally include one or more slide mechanisms 154. In the embodiment shown in FIG. 4A, the compressor system has two slide mechanisms 154A, 154B. A first slide mechanism 154A is coupled to the first outer hub 144A and is configured to slide the first plurality of blades 112A along the central axis A independently of the second plurality of blades 112B and the second slide mechanism 154B is configured to slide the second plurality of blades 112B along the axis A independently of the first plurality of blades 112A.

A slide mechanism may comprise a transfer mechanism 156, as shown in FIG. 4B, that translates rotational movement into linear movement. The transfer mechanism 156 may include first and second levers 157A, 157AA. One end of each lever 157A, 157AA includes an engagement member 158A, 158AA that engages the outer hub 144A along an axis A1 perpendicular to the central axis A. A tie bar 159 couples the levers along an axis A2 parallel to A1. Rotation of tie bar 159 causes the first plurality of blades 112A to move along the axis A. Because the first and second pluralities of blades 112A, 112B are decoupled, the blades 112A, 112B can move independently of one another.

Various new and useful applications for compressors of the present invention will now be described. In FIG. 6A, a compressor of the present invention is shown and includes a blade array 110 comprising a first plurality of blades 112A and a second plurality of blades 112B. The blades 112A, 112B are shown in an expanded configuration. An expandable medical device 120, for example a self-expanding stent, is disposed within the aperture 115 of the blade array 110 and is shown in an expanded configuration. A sheath 160 is provided for receiving and retaining the stent 120 in a contracted configuration. The lumen 162 of the sheath 160 may be positioned in alignment with the central axis A. The sheath 160 has an inner diameter that is generally equal to or slightly larger than the contracted diameter of the stent 120.

Figure 6B:
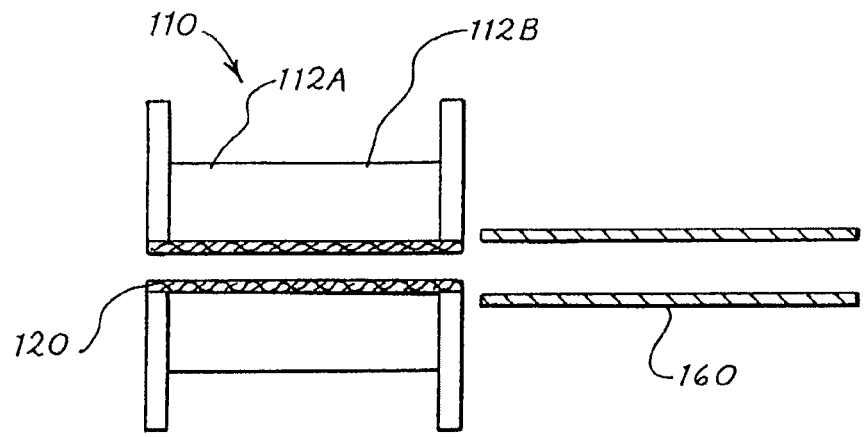

In FIG. 6B, the blades 112A, 112B have moved from the expanded configuration of FIG. 6A to a contracted configuration. The first and second pluralities of blades 112A, 112B compress and hold the expandable stent 120 in a contracted configuration.

At this point, a pushing device (not shown) may be provided for pushing the compressed stent 120 into the sheath 160. The pushing device may engage an end of the stent 120 and push the stent towards the sheath 160 and into the sheath lumen 162. The pushing device must apply sufficient force to overcome any frictional resistance between the blades 112A, 112B and the stent 120. If the stent 120 is particularly flexible, or if it is sufficiently long, the force required to overcome the frictional resistance may be greater than the column strength of the stent 120. In either case, the pushing device may cause the stent 120 to longitudinally compress, buckle, or crush.

Figure 6C:
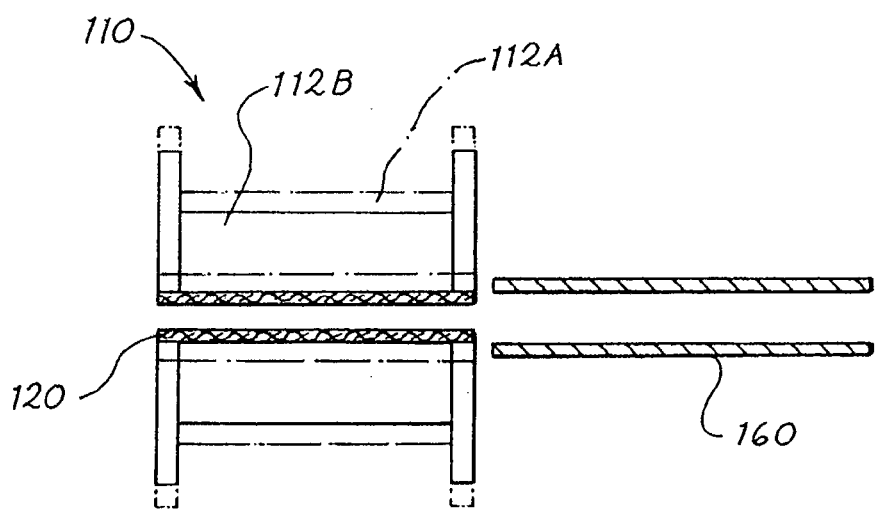

In FIG. 6C, the first plurality of blades 112A has moved radially away from the stent 120 and is shown in a retracted configuration. The first plurality of blades 112A is disengaged from the stent 120 and the stent is held in a contracted configuration by the second plurality of blades 112B.

Because the first plurality of blades 112A is no longer in contact with the stent 120, the area of frictional contact between the blade array 110 and the stent 120 is reduced. Accordingly, the friction between the blades 112A, 112B and the stent 120 will be reduced. A pusher (not shown) may be provided at this point to push the stent 120 into the sheath 160. Because friction has been reduced, the stent 120 is less likely to compress, buckle, or crush under the force of the pusher.

The compressor system may be operated so that the first plurality of blades 112A alternately engages and disengages the stent 120 and the second plurality of blades 112B alternately disengages and engages the stent 120. Repetitively engaging and disengaging blades 112A and repetitively disengaging and engaging blades 112B may reduce the surface contact area between the blades 112A, 112B at any given time, and may reduce the effects of static friction between the blades and the stent 120. The frequency with which the blades 112A, 112B engage and disengage the stent 120 may vary. For example, the first and second pluralities of blades 112A, 112B may move between engaged and disengaged configurations at a rate of once per second. The frequency may be more or less depending on the desired effect. The first and second outer hubs 144A, 144B may be controlled to engage and disengage the stent 120 using a standard input/output device, for example, a computer.

It is important to note that the blades 112A, 112B need only move away from the stent a distance that is necessary to disengage the blades from the stent 120. In many cases, it may only be necessary to move the blades as little as ten thousandths of an inch from the stent 120 in order to effect frictional disengagement.

Other methods of compressing and loading an expandable medical device into a sheath are contemplated. A preferred method may be described with reference to FIGS. 6A-6G and 7A-7G and with respect to the exemplary compressor system shown in FIGS. 4A-4C and described above. In FIG. 6A, the blade array 110 is shown with the first and second pluralities of blades 112A, 112B in an expanded configuration. A stent 120 is placed within the aperture 115 of the blade array 115. FIG. 7A illustrates the relative positions of the blades 112A, 112B in the expanded configuration. A sheath 160 is provided and is aligned with the axis A so that the sheath lumen 162 is positioned to receive the stent 120 in the contracted configuration.

The blade array 110 contracts and the stent 120 is compressed, for example, by rotating the inner hubs 124A, 124B of the compressor of FIGS. 4A-4C while holding the outer hubs 144A, 144B stationary. In FIG. 6B, the blade array is shown in a contracted configuration. The stent 120 is compressed into a contracted configuration and the first and second pluralities of blades 112A, 112B engage the stent. As shown in FIG. 7B, each of the blades 112A, 112B moves radially inwardly along an arc between the expanded and contracted configurations.

Next, the first plurality of blades 112A disengages and retracts from the stent 120 while the second plurality of blades 112B holds the stent. This may be done via rotation of the first outer hub 144A with respect to the second outer hub 144B. In FIG. 6C, the first plurality of blades 112A is moved radially outwardly with respect to the second plurality of blades 112B. The configuration of the blades 112A, 112B is shown in 7C.

Each of the first plurality of blades 112A moves radially outwardly along an arc between the contracted and retracted configurations.

Figure 6D:
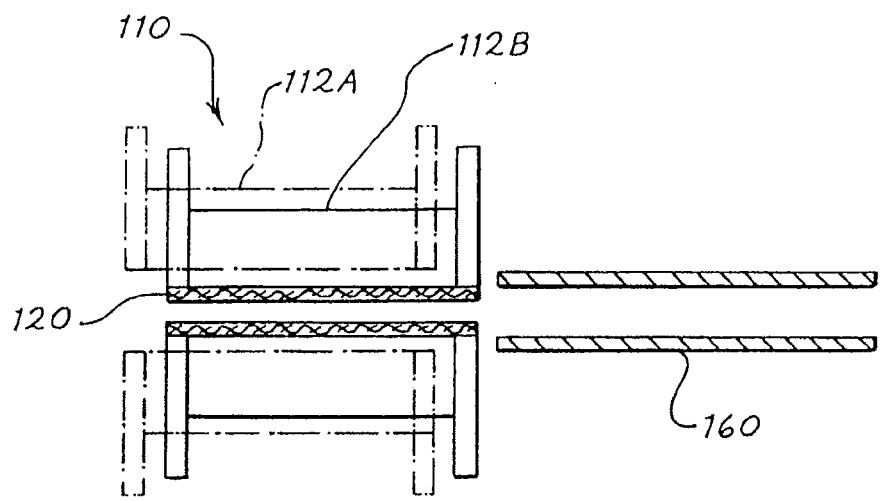
Figure 7C:
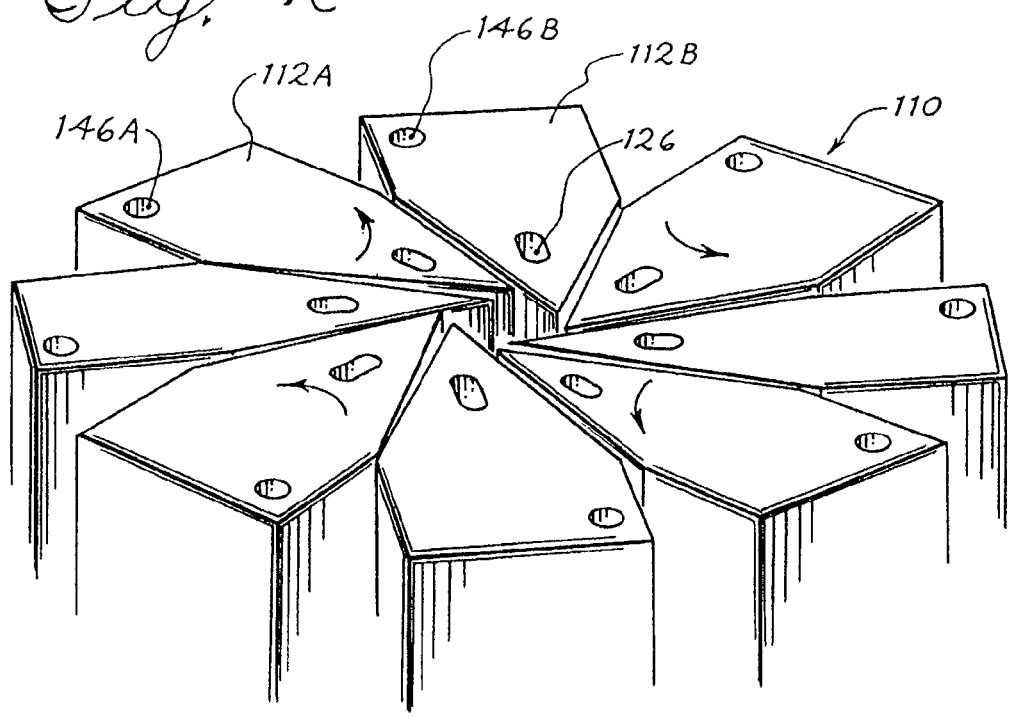
Figure 7D:
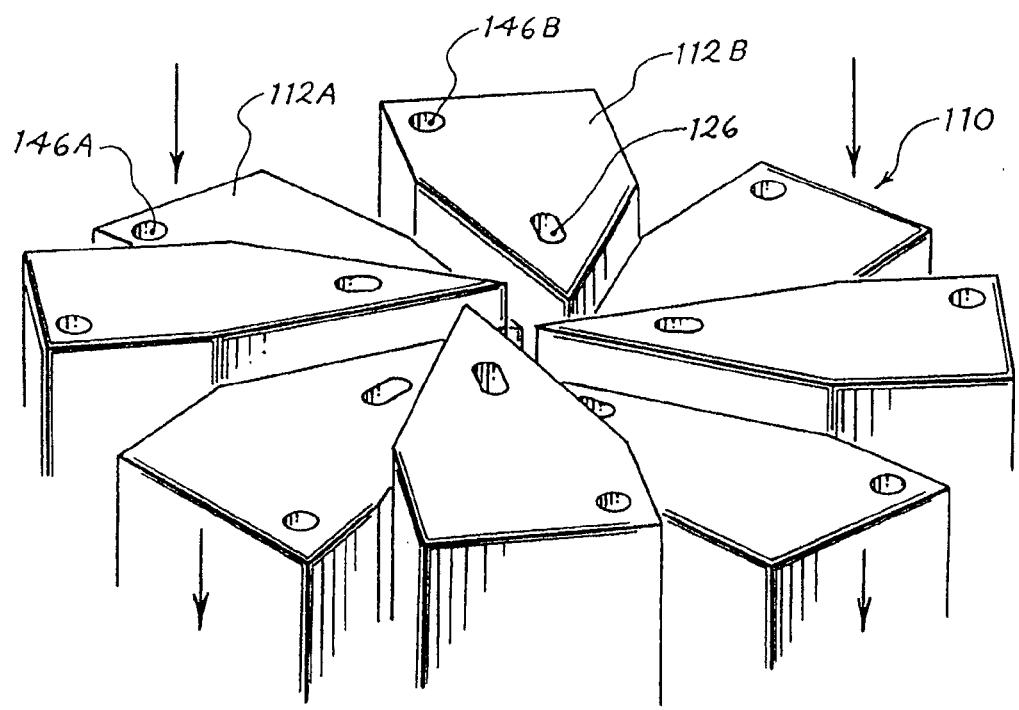

In FIG. 6D, the first plurality of blades 112A has moved along the axis A away from the sheath 160 while the second plurality of blades 112B remains stationary. The blades 112A may be moved by actuating the first sliding mechanism 154A. At this point, the stent 120 is still held by the second plurality of blades 112B. The configuration of the blades 112A, 112B is shown in FIG. 7D.

Figure 6E:
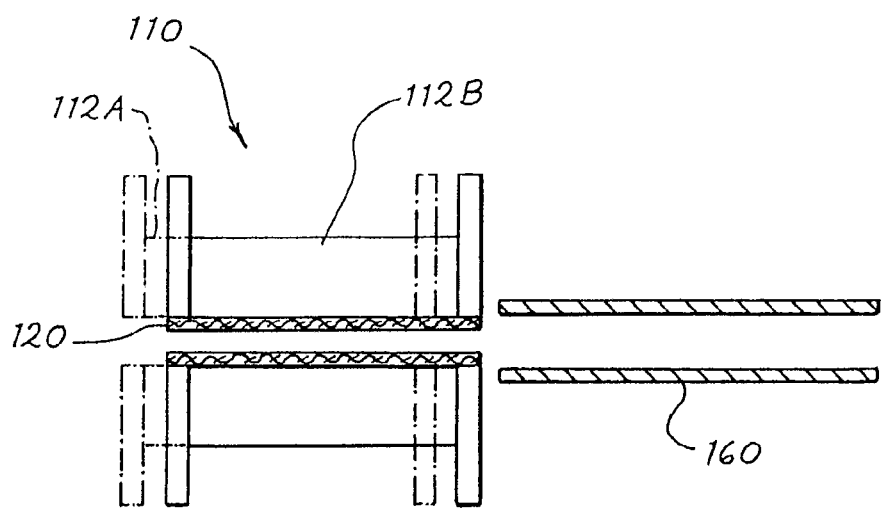
Figure 7E:
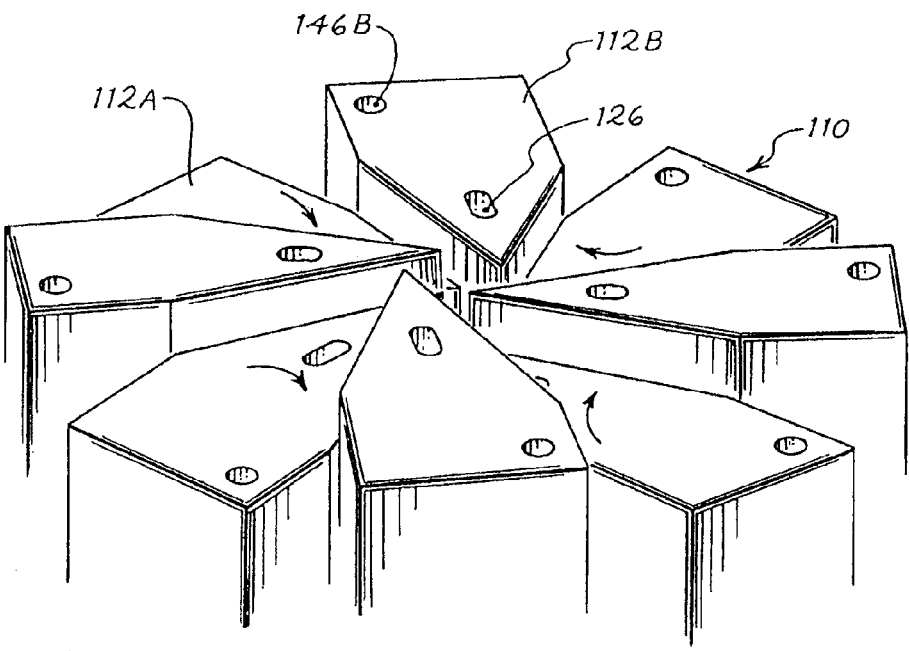

Next, the first plurality of blades 112A engages the stent 120, for example, by rotating the first outer hub 144A while holding the second outer hub 144B stationary. In this step, the first outer hub 144A is rotated in a direction that is opposite the direction of rotation in the disengagement step of FIG. 6C. The first plurality of blades 112A moves radially inwardly with respect to the second plurality of blades 112B. The stent 120 is now held by both the first and second pluralities of blades 112A, 112B, as shown in FIGS. 6E and 7E.

Figure 6F:
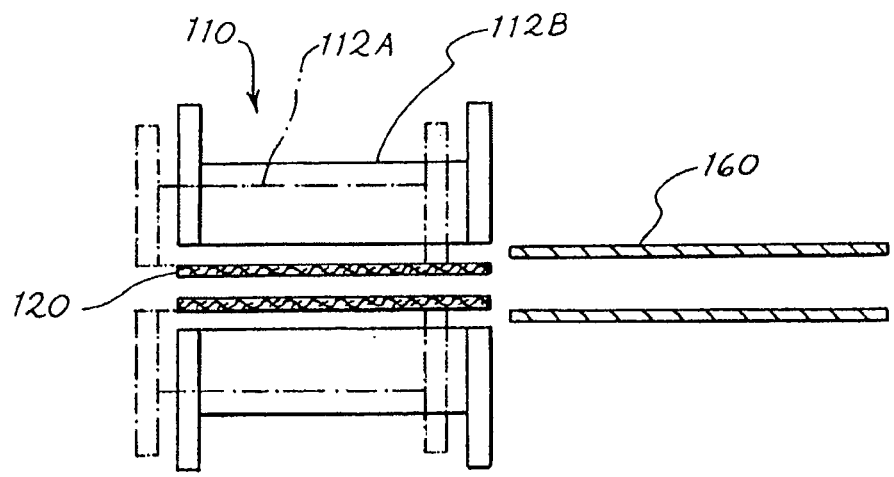
Figure 7F:
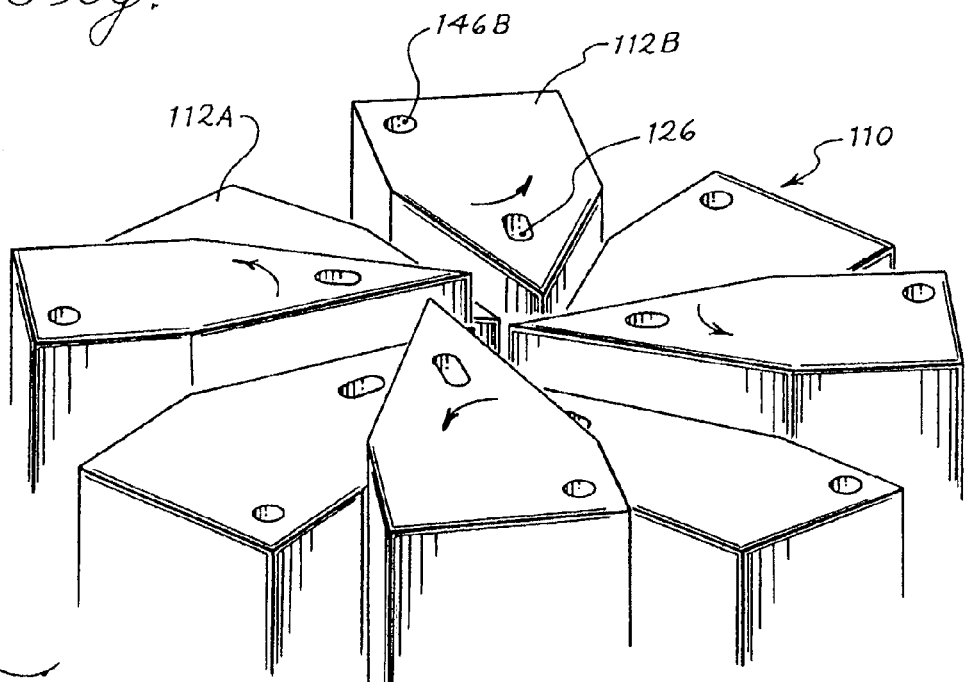

Next, as shown in FIGS. 6F and 7F, the second plurality of blades 112B disengages and retracts from the stent 120 while the stent is held in the contracted configuration by the first plurality of blades 112A, for example, by rotating the second outer hub 144B with respect to the first outer hub 144A. Each of the second plurality of blades 112B moves radially outwardly along an arc between the contracted and the retracted configurations.

Figure 6G:
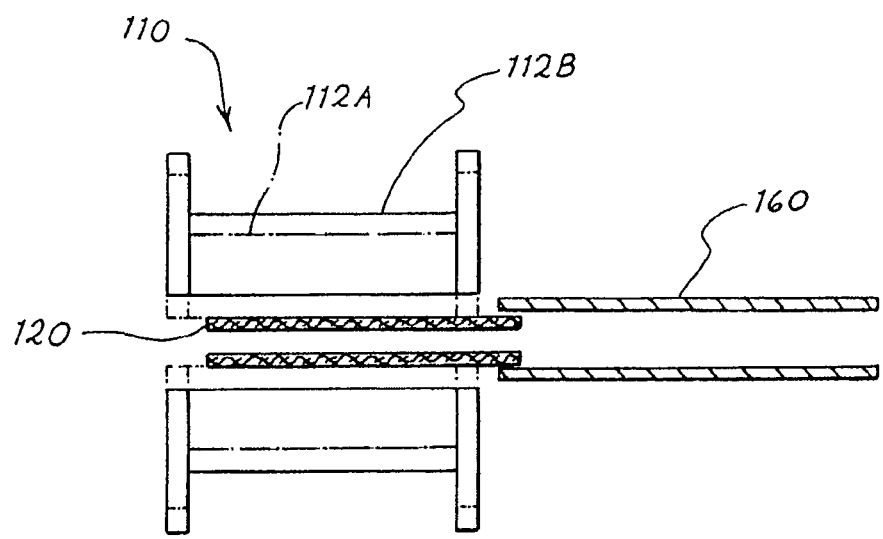
Figure 7G:
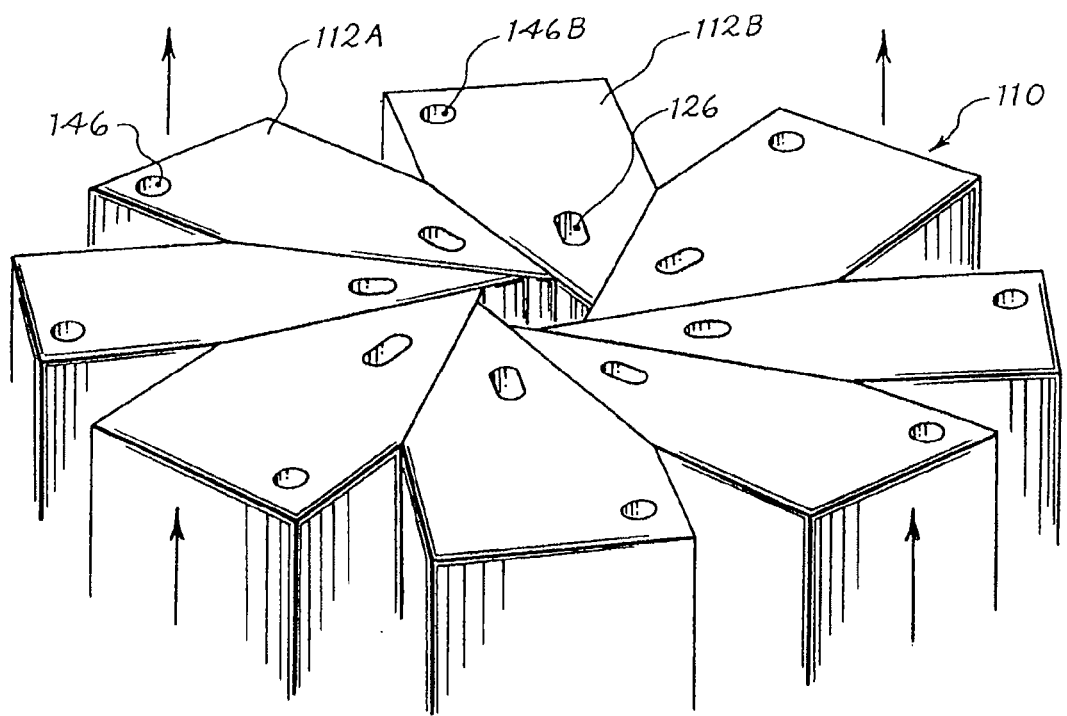

In FIGS. 6G and 7G, the first plurality of blades 112A has moved along the axis A towards the sheath 160 while the second plurality of blades 112B remains stationary. The blades 112A may be moved by actuating the first sliding mechanism 154A. Because the first plurality of blades 112A engages the stent 120, the stent moves with the blades towards the sheath 160. After this step, the blades may return to the configuration shown in FIGS. 6B and 7B, for example, by rotating the second outer hub 144B while holding the first outer hub 144A stationary, thereby reengaging the second plurality of blades 112B with the stent.

Alternatively, at this point, the second plurality of blades 112B may be moved along the axis A away from the sheath 160 while holding the first plurality of blades 112A stationary, for example, using the second sliding mechanism 154B. The second plurality of blades 112B may then reengage the stent 120 and the first plurality of blades 112A may disengage from the stent 120 while the device is held by the second plurality of blades 112B. Next, using the second sliding mechanism 154B, the second plurality of blades 112B may be moved along the axis A towards the sheath 160 while holding the first plurality of blades stationary to advance the stent 120 further into the sheath.

It will be apparent that many combinations and permutations of the steps recited above may be performed and repeated successively, as required, to completely transfer the stent 120 into the lumen of the sheath 160, with or without the need for a pusher.

The compressor blades may engage a medical device by various means, including, but not limited to, mechanical interaction between the blades and the device. For example, the blades may engage the medical device merely via frictional contact. According to an aspect of the invention, at least one of the first and second plurality of blades may be treated to selectively increase the friction between the treated blades and the medical device. For example, the blades may comprise a rough or textured surface finish. The surface finish may be provided, for example, by sand blasting or laser etching, or the surface finish may comprise a textured coating.

Alternatively, at least one of the first and second plurality of blades may be treated to selectively decrease the friction between the blades and the medical device. For example, the blades may comprise a smooth surface finish. The surface finish may be provided by mechanical means including by polishing. Alternatively, a smooth or lubricious coating may be applied to the blade surface. Other engagement structures and devices are contemplated and are within the scope of the invention. For example, the blades may be provided with structures or details that are configured to engage with corresponding structures or details of the medical device.

Figure 8:
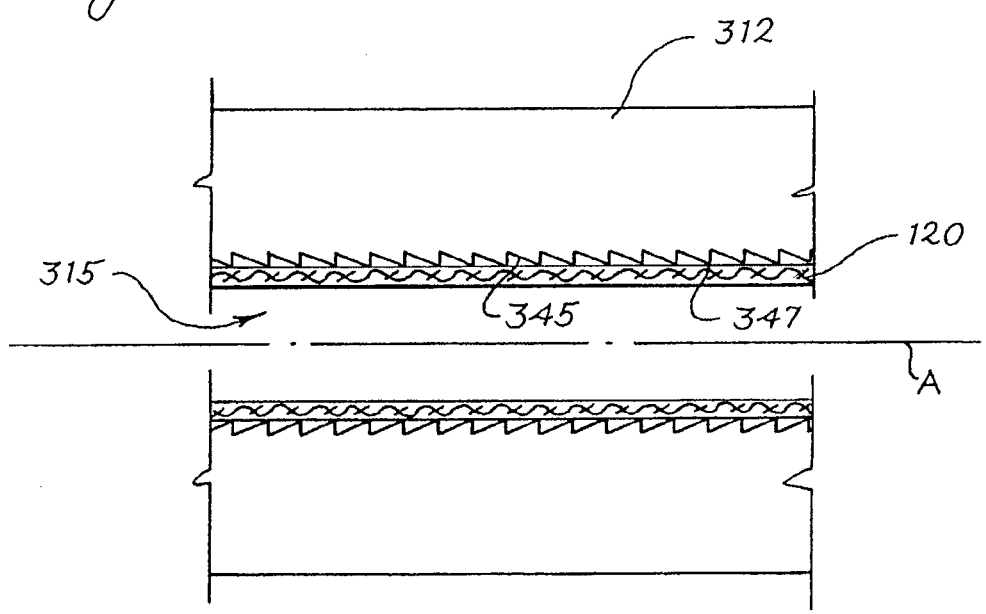
FIG. 8 is a partial cross-section of a stent held within compressor blades that have a selective engagement interface according to an aspect of the invention.

According to another aspect of the invention, the blades may be configured to engage the medical device when the blades slide in a first direction and to disengage the device when the blades slide in a second, opposite direction. FIG. 8 shows a stent 120 compressed within the aperture 315 formed by a plurality of blades 312. Blades 312 have a selective engagement interface. The surface of blades 312 includes a plurality of longitudinally oriented asymmetric ridges 345. Ridges 345 have apices 347 that are oriented in a first direction with respect to the central axis A, forming a saw-tooth pattern. The ridges 345 are configured so that when the stent 120 is compressed and the blades 312 slide in the first direction, the blades 312 engage the stent 120. Conversely, when the blades 312 slide in the second direction, the blades 312 disengage from the stent 120.

A compressor system according to the present invention may be provided wherein the second plurality of blades 112B is treated to minimize frictional resistance with a medical device and the first plurality of blades 112A is treated to maximize frictional resistance with the device. Accordingly, the apparatus could be operated to advance the device as described above. If the friction between the first plurality of blades 112A and the stent is sufficiently greater than the friction between the second plurality of blades 112B and the stent, the first plurality of blades 112A may be able to move the device without having to retract the second plurality of blades 112B from the device.

In another embodiment, a compressor system may be provided wherein each of the first plurality of blades 112A and the second plurality of blades 112B includes a selective engagement interface. The blades are configured so that the first plurality of blades 112A engages the medical device and the second plurality of blades 112B disengages from the medical device when the first plurality of blades moves in a first direction with respect to the second plurality of blades. Conversely, the blades are configured so that the first plurality of blades 112A disengages from the medical device and the second plurality of blades 112B engages the medical device when the first plurality of blades 112A moves in a second opposite direction with respect to the second plurality of blades. Accordingly, when the first plurality of blades 112A moves in the first direction with respect to the second plurality 112B, the device will move in the first direction, and when the first plurality of blades 112A moves in the second direction with respect to the second plurality 112B, the device will remain stationary. It will be immediately apparent that as configured, it will not be necessary to retract any of the blades 112A, 112B from the stent during operation.

Throughout this specification various indications have been given as to preferred and alternative embodiments of the invention. However, it should be understood that the invention is not limited to any one of these. It is therefore intended that the foregoing detailed description be regarded as illustrative rather than limiting, and that it be understood that it is the appended claims, including all equivalents, that are intended to define the spirit and scope of this invention.

The invention claimed is:

1. A system for compressing a medical device comprising:
a plurality of moveable blades disposed about a central axis and forming an iris that defines a radially contractible aperture, the blades being configured to receive and compress a medical device within the aperture; and
an operating mechanism for moving the plurality of blades between an expanded configuration and a contracted configuration;
wherein a subset of the plurality of blades is independently moveable in at least a first axial direction with respect to other of the plurality of blades while the plurality of blades are in a contracted configuration.

2. The system according to claim 1, wherein said subset of the plurality of blades is independently moveable in at least the first axial direction while said other of the plurality of blades are stationary.

3. The system according to claim 2, wherein the compressed medical device is moved a second, opposite axial direction within the aperture when said subset of the plurality of blades is moved in the second axial direction.

4. The system according to claim 3, wherein the medical device is moved in the second axial direction without retracting said other of the plurality of blades from the device.

5. The system according to claim 4, wherein the medical device is moved in the second axial direction without retracting any of the plurality of blades from the device.

6. The system according to claim 5, wherein at least one of said subset of the plurality of blades and said other of the plurality of blades is treated to decrease the friction between the blades and the medical device.

7. The system according to claim 5, wherein the blades are configured to disengage the medical device when the blades slide in the first axial direction and to engage the medical device when the blades slide in the second, opposite axial direction.

8. A system for compressing and loading a self-expanding medical device into a sheath comprising:
a plurality of moveable blades disposed about a central axis and forming an iris that defines a radially contractible aperture, the blades being configured to receive and compress a medical device within the aperture;
an operating mechanism for moving the plurality of blades between a radially expanded configuration and a radially contracted configuration; and
an operating mechanism for moving some of the plurality of blades in a first axial direction with respect to other of the plurality of blades while the plurality of blades are in a radially contracted configuration;
wherein the compressed medical device is moved in a second, opposite axial direction within the aperture when said some of the plurality of blades are moved in the second axial direction.

9. The system according to claim 8, wherein the medical device is moved in the second axial direction without retracting said other of the plurality of blades from the device.

10. The system according to claim 9, wherein the medical device is moved in the second axial direction without retracting any of the plurality of blades from the device.

11. The system according to claim 10, wherein the blades disengage the medical device when the blades slide in the first axial direction and engage the medical device when the blades slide in the second axial direction.

12. A method of operating a compressor for compressing a medical device, the compressor comprising at least a first group of blades radially disposed about a central axis and a second group of blades radially disposed about the central axis, the first group of blades and the second group of blades arranged to be axially coextensive, the method comprising:
moving the first and second groups of blades between a radially expanded configuration and a radially contracted configuration to compress the medical device; and
selectively moving the first group of blades independently with respect to the second group of blades.

13. The method according to claim 12, wherein the first group of blades is moved in at least a first axial direction with respect to the second group of blades.

14. The method according to claim 13, wherein the first group of blades is moved in the first axial direction with respect to the second group of blades while the plurality of blades are in the contracted configuration.

15. The method according to claim 14, wherein the medical device is moved in a second, opposite axial direction within the aperture when the first group of blades is moved in the second axial direction.

16. The method according to claim 15, wherein the medical device is moved in the second axial direction without retracting the second group of blades from the device.

17. The method according to claim 16, wherein the medical device is moved in the second axial direction without retracting any of the plurality of blades from the device.

18. The method according to claim 12, further comprising:
providing a sheath for receiving and retaining the medical device in a contracted configuration;
positioning the sheath in alignment with the central axis; and
pushing, with a pushing device, the compressed medical device out of the aperture and into the sheath.

19. The method according to claim 12, wherein the groups of blades are circumferentially interleaved.

20. The method according to claim 19, wherein the total number of blades is 12 or more and the number of blades in each group is 3 or more.

* * * * *